(12) United States Patent
Dillingham

(10) Patent No.: US 8,470,050 B2
(45) Date of Patent: Jun. 25, 2013

(54) RAPID FIT MODULAR PROSTHETIC DEVICE FOR ACCOMMODATING GAIT ALIGNMENT AND RESIDUAL LIMB SHAPE AND VOLUME

(76) Inventor: Timothy R. Dillingham, Merion Station, PA (US)

( * ) Notice: Subject to any disclaimer, the term of this patent is extended or adjusted under 35 U.S.C. 154(b) by 58 days.

(21) Appl. No.: 13/274,130

(22) Filed: Oct. 14, 2011

(65) Prior Publication Data

US 2012/0259434 A1 Oct. 11, 2012

Related U.S. Application Data

(63) Continuation-in-part of application No. 13/083,403, filed on Apr. 8, 2011.

(51) Int. Cl.
*A61F 2/80* (2006.01)
*A61F 2/78* (2006.01)

(52) U.S. Cl.
USPC .............................................. 623/36; 623/33

(58) Field of Classification Search
USPC ..................................................... 623/33, 36
See application file for complete search history.

(56) References Cited

U.S. PATENT DOCUMENTS

| | | | |
|---|---|---|---|
| 1,090,881 A | 3/1914 | Rowley | |
| 4,161,042 A | 7/1979 | Cottingham et al. | |
| 4,302,856 A | 12/1981 | May | |
| 4,872,879 A | 10/1989 | Shamp | |
| 5,314,497 A | 5/1994 | Fay et al. | |
| 5,425,782 A | 6/1995 | Phillips | |
| 5,443,526 A | 8/1995 | Hoerner | |
| 5,529,575 A | 6/1996 | Klotz | |
| 5,571,209 A | 11/1996 | Brown, Sr. | |
| 5,651,792 A | 7/1997 | Telikicherla | |
| 5,728,165 A | 3/1998 | Brown, Sr. | |
| 5,728,170 A | 3/1998 | Becker et al. | |
| 5,888,234 A | 3/1999 | Littig | |
| 5,941,912 A | 8/1999 | Taylor et al. | |
| 6,051,026 A | 4/2000 | Biedermann et al. | |
| 6,267,787 B1 | 7/2001 | Capper et al. | |
| 6,398,817 B1 | 6/2002 | Hellberg et al. | |
| 6,689,171 B2 | 2/2004 | Slemker et al. | |
| 6,942,703 B2 | 9/2005 | Carstens | |
| 6,991,657 B1 | 1/2006 | Price, Jr. | |
| 7,083,654 B2 | 8/2006 | Helenberger et al. | |
| D617,460 S | 6/2010 | Okuda et al. | |

(Continued)

FOREIGN PATENT DOCUMENTS

| | | |
|---|---|---|
| GB | 2169207 A | 7/1986 |
| GB | 2274994 A | 8/1994 |
| JP | 08089519 A | 4/1996 |
| RU | 2088182 C1 | 8/1997 |

OTHER PUBLICATIONS

JP 7-155343 A (Jun. 20, 1995) English language translation.
Office Action issued on Apr. 16, 2013 in related U.S. Appl. No. 13/274,146.

(Continued)

*Primary Examiner* — David H Willse

(57) ABSTRACT

A Rapid Fit Modular Prosthetic Device that can be inexpensively manufactured using modern technology and advanced polymer materials. The Rapid Fit Modular Prosthetic Device will be immediately fit on the residual limb and aligned for optimal gait without specialized tools or labs, alleviating the many steps involved with conventional labor-intensive and costly prosthesis construction. The Rapid Fit Modular Prosthetic Device also accommodates the changing in size and shape of the limb, eliminating the need for multiple prostheses and adjustments to an existing prosthesis during the lifetime of an amputee.

20 Claims, 11 Drawing Sheets

U.S. PATENT DOCUMENTS

| | | |
|---|---|---|
| 2002/0116789 A1 | 8/2002 | McDevitt |
| 2003/0023320 A1 | 1/2003 | Laghi |
| 2003/0233151 A1 | 12/2003 | Lund |
| 2005/0271462 A1 | 12/2005 | Curtis |
| 2005/0278038 A1 | 12/2005 | Ikeda |
| 2007/0260328 A1 | 11/2007 | Bertels et al. |
| 2009/0043402 A1 | 2/2009 | Slemker |
| 2010/0036505 A1 | 2/2010 | Hassler |
| 2010/0274364 A1 | 10/2010 | Pacanowsky et al. |
| 2011/0015761 A1 | 1/2011 | Celebi et al. |
| 2011/0071647 A1 | 3/2011 | Mahon |

OTHER PUBLICATIONS

Notice of Allowance issued on Apr. 15, 2013 in related U.S. Appl. No. 13/083,403.

Office Action issued on Feb. 22, 2013 in related U.S. Appl. No. 13/083,403.

Written Opinion and International Search Report issued Mar. 29, 2013 in related International Patent Application No. PCT/US2012/060168.

Written Opinion and International Search Report issued Mar. 15, 2013 in related International Patent Application No. PCT/US2012/060166.

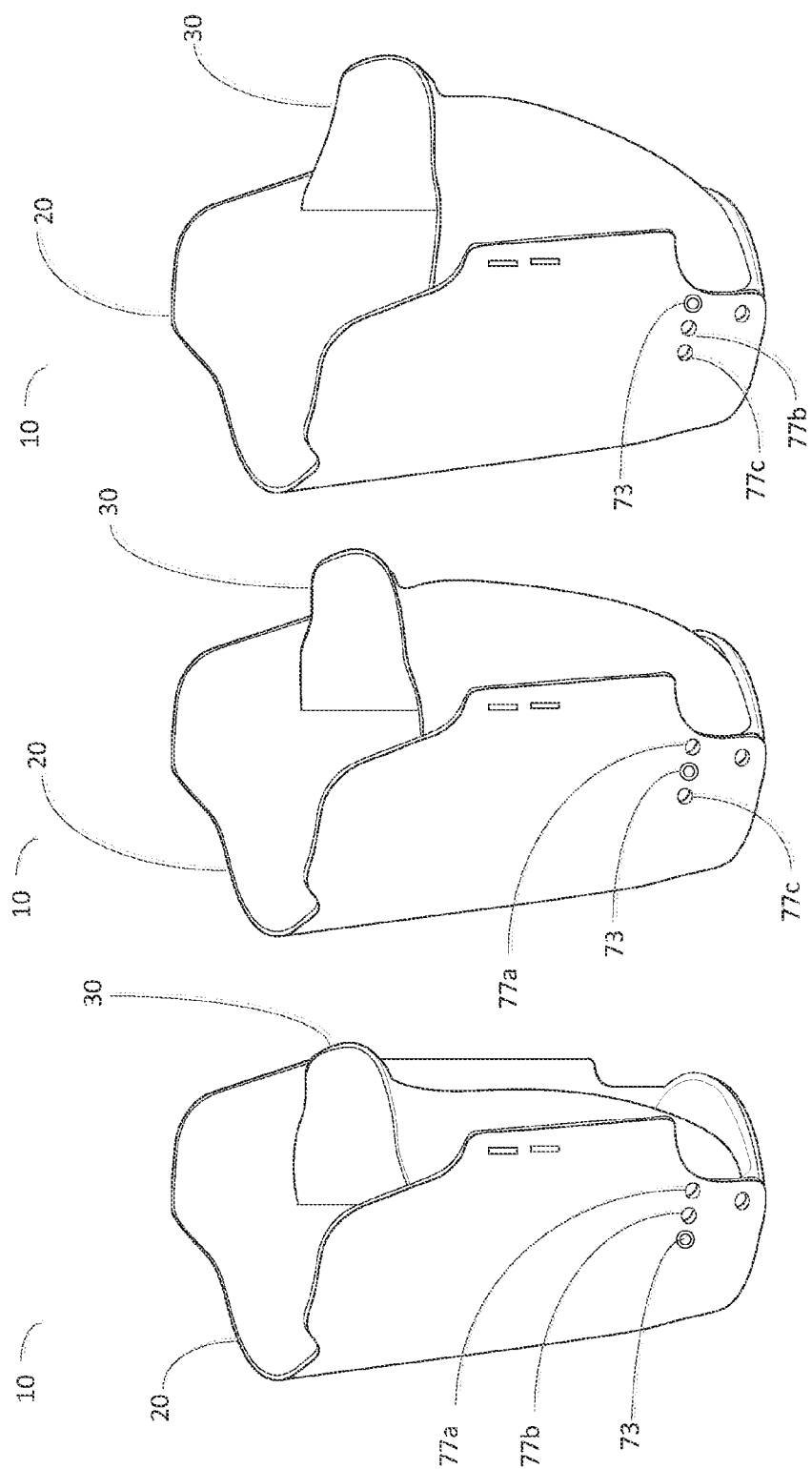

United States Patent US 8,470,050 B2

RAPID FIT MODULAR PROSTHETIC DEVICE FOR ACCOMMODATING GAIT ALIGNMENT AND RESIDUAL LIMB SHAPE AND VOLUME

CROSS-REFERENCE TO RELATED APPLICATION

This application is a continuation-in-part of U.S. patent application Ser. No. 13/083,403 entitled "Modular Prosthesis System," filed on Apr. 8, 2011, which is hereby incorporated by reference in its entirety.

STATEMENT REGARDING FEDERALLY SPONSORED RESEARCH OR DEVELOPMENT

This invention was made with government support under NIH Grant 2R42HD069067-02 awarded by the National Institutes of Health. The government has certain rights in the invention.

FIELD OF INVENTION

The present invention relates to the field of prostheses, and more particularly to a modular prosthesis system which accommodates gait alignment and residual limb shape and volume.

BRIEF DESCRIPTION OF THE DRAWINGS

FIGS. 5a, 5b, 5c illustrate the adjustability of an exemplary embodiment of a rear limb engaging member for a rapid fit modular prosthetic device for accommodating gait alignment and residual limb shape and volume.

GLOSSARY

Figure 1:
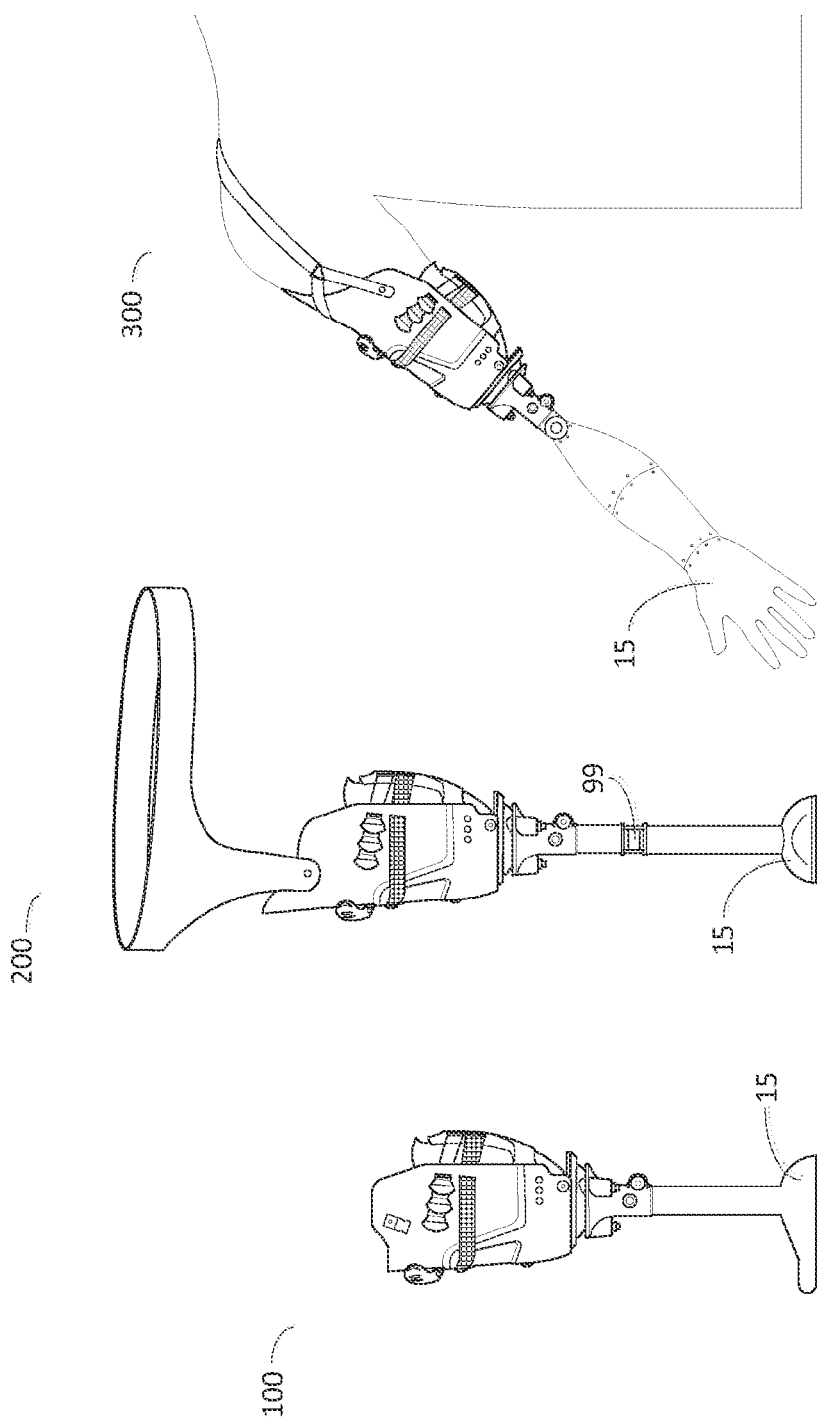
FIG. 1a illustrates an exemplary embodiment of a rapid fit modular prosthetic device for accommodating gait alignment and residual limb shape and volume for a below-the-knee residual limb.
FIG. 1b illustrates an exemplary embodiment of a rapid fit modular prosthetic device for accommodating gait alignment and residual limb shape and volume for an above-the-knee residual limb.
FIG. 1c illustrates an exemplary embodiment of a rapid fit modular prosthetic device for accommodating gait alignment and residual limb shape and volume for a residual limb which is an arm.

As used herein, the term "deformable" means any structure with accommodating features for comfort and/or to reduce impact. Deformable materials may include, but are not limited to, padding, foam, cushioning, gel, rubber and any other malleable, moldable or adjustable material or combinations of materials known in the art.

As used herein, the term "flexible" means able to bend repeatedly without damage or breaking.

BACKGROUND

Over 150,000 amputations occur in the United States annually. Amputations are rising in frequency due to diabetes and peripheral vascular disease. The transtibial level of amputation is the most frequently performed.

A transtibial amputation is an amputation of the lower limb below the knee. A transtibial prosthesis is an artificial limb that replaces the portion of the leg below the knee that is missing. The shape of the residual limb varies for each individual and generally requires a custom-filled prosthesis. A custom-fitted prosthesis that is comfortable is difficult to fabricate and costly.

The initial cost of a conventional prosthesis for a transtibial amputee typically ranges from $6000 to $14,000. In addition, there are additional costs to ensure the comfort and functionality of the device. The present state of prosthesis fabrication often requires three or more visits to the prosthetist and there are multiple steps in the fabrication process. First, a cast mold of the residual limb is made and a positive cast that resembles the residual limb is generated. Then, a prosthetic socket is built to custom-fit over the positive cast. Sometimes a check or temporary socket is made to insure a better fit. Typical fabrication techniques require specialized facilities. Generally, the final prosthesis requires post-fabrication adjustments as the residual limb tissue changes over time.

Recent advancements have been made in the field of prosthetic devices. However, devices such as computerized knee mechanisms and energy storing feet are costly and beyond the economic means of the majority of prosthetic users, particularly those in nations outside the United States.

Attempts have been made in the prior art to develop prosthesis systems that can be globally manufactured and distributed. These prosthesis systems, however, have several limitations. They are difficult to fabricate and require specialized facilities for initial manufacturing (e.g., casting) and subsequent adjustments. These systems all require expertise and consulting support that is not widely available. In particular, the socket (i.e., the portion of the prosthesis into which the residual limb fits), socket attachment, and alignment aspects of the device seem to be a common problematic area of development.

It is desirable to create a prosthetic device which eliminates the need for complex fabrication and specialized tools or labs, and which can be economically manufactured and distributed on a global basis.

Residual limbs may also grow or otherwise change shape, which may occur rapidly. In some instances, it may be necessary to replace a prosthetic device every six months to a year. It is desirable to create a prosthetic device which is adjustable to provide continued support and comfort as a residual limb changes.

SUMMARY OF THE INVENTION

A rapid fit nodular prosthetic apparatus contains a rigid socket assembly, including a deformable liner, and fitted base component containing a first convex plate base and a concave base plate. A securing strap assembly, including a looped cable and a securing strap, secure a residual limb in the rigid socket assembly. The rigid socket assembly is connected to the first convex plate base, which is joined to the concave base plate by a plurality of rocker bolt assemblies. The rocker bolts allow adjustment of the shank and foot relative to the socket. Once the optimal alignment is achieved, the rocker bolts are tightened to firmly connect the upper and lower plates such that no movement occurs during gait. A hollow tubular portion of the fitted base component receives a prosthetic pipe, or shank, that is connected to a prosthetic foot.

A rapid fit modular prosthetic apparatus may be used on below-the-knee and above-the-knee residual limbs, as well as residual limbs which are arms. Additional securing components, such as waist straps or shoulder straps, may be used in above-the-knee and arm embodiments.

DETAILED DESCRIPTION OF INVENTION

For the purpose of promoting an understanding of the present invention, references are made in the text to exemplary embodiments of a rapid fit modular prosthetic device for accommodating gait alignment and residual limb shape and volume, only some of which are described herein. It should be understood that no limitations on the scope of the invention are intended by describing these exemplary embodiments. One of ordinary skill in the art will readily appreciate that alternate but functionally equivalent materials, component, and designs may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the varios drawings refer to identical or near identical structural elements.

Moreover, the terms "substantially" or "approximately" as used herein may be applied to modify any quantitative representation that could permissibly vary without resulting in a change in the basic function to which it is related.

FIGS. 1a, 1b and 1c illustrate three different uses of a rapid fit modular prosthetic device for accommodating gait alignment and residual limb shape and volume. As illustrated in FIG. 1a, rapid fit modular prosthetic device for accommodating gait alignment and residual limb shape and volume 100 is adapted for use on a below-the-knee residual limb. As illustrated in FIG. 1b, rapid fit modular prosthetic device for accommodating gait alignment and residual limb shape and volume 200 may also be adapted for use with an above-the-knee residual limb. FIG. 1c illustrates rapid fit modular prosthetic device for accommodating gait alignment and residual limb shape and volume 300 adapted for use with a residual limb which is an arm.

As illustrated in FIGS. 1a, 1b and 1c, the basic structure of rapid fit modular prosthetic device for accommodating gait alignment and residual limb shape and volume 100, 200, 300 is the same. Rapid fit modular prosthetic device for accommodating gait alignment and residual limb shape and volume 100 has prosthetic device 15 attached directly to rapid fit modular prosthetic device for accommodating gait alignment and residual limb shape and volume 100. By comparison, rapid fit modular prosthetic device for accommodating gait alignment and residual limb shape and volume 200 has knee 99 after prosthetic device 15 and an additional securing strap to help stabilize rapid fit nodular prosthetic device for accommodating gait alignment and residual limb shape and volume 200. The orientation of prosthetic limb 15 is also rotated at 90 degrees compared to rapid fit modular prosthetic device for accommodating gait alignment and residual limb shape and volume 100.

When used for a below-the-knee residual limb, rapid fit modular prosthetic device for accommodating gait alignment and residual limb shape and volume 100 is oriented so that it opens from the back of a wearer (i.e., at the calf). Because of the way pressure is exerted on rapid fit modular prosthetic device for accommodating gait alignment and residual limb shape and volume 200 when used with an above-the-knee residual limb, and the movement caused by bending at the knee, rapid fit modular prosthetic device for accommodating gait alignment and residual limb shape and volume 200 must be oriented to open from the side.

Similarly, as illustrated in FIG. 1c, rapid fit modular prosthetic device for accommodating gait alignment and residual limb shape and volume 300 contains a different strap to secure rapid fit modular prosthetic device for accommodating gait alignment and residual limb shape and volume 300 to a residual limb which is an arm, and prosthetic device 15 is an arm instead of a foot or leg.

Figure 2:
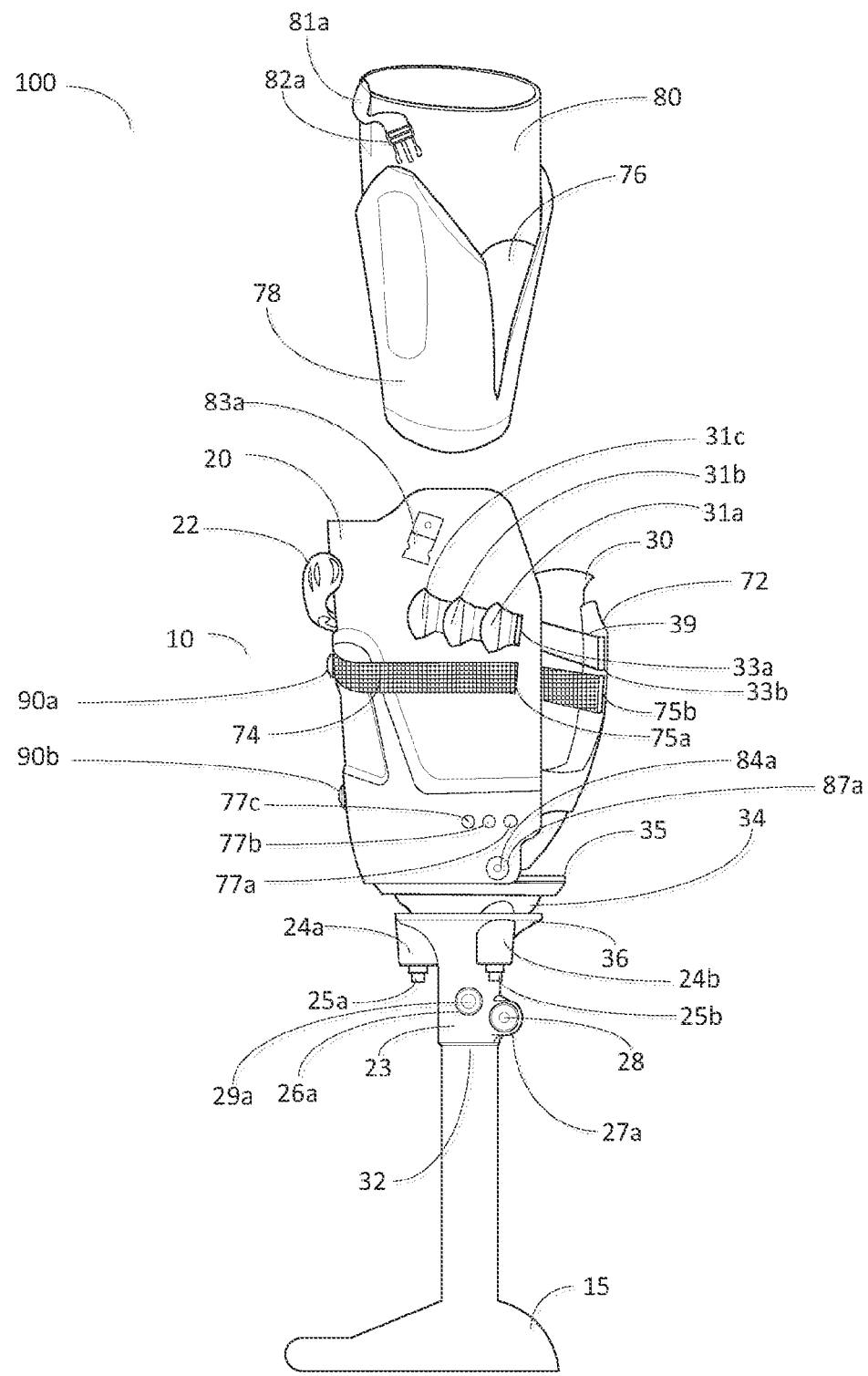
FIG. 2 illustrates an exemplary below-the-knee rapid fit modular prosthetic device for accommodating gait alignment and residual limb shape and volume.

FIG. 2 illustrates an exemplary embodiment of below-the-knee rapid fit modular prosthetic device for accommodating gait alignment and residual limb shape and volume 100. Below-the-knee rapid fit modular prosthetic device for accommodating gait alignment and residual limb shape and volume 100 contains rigid socket assembly 10, which is comprised of non-pivotal front limb engaging panel 20, pivotal rear limb engaging panel 30, rigid outer support rib 72, and deformable inner liner 78 with silicone sleeve 80. In the exemplary embodiment shown, rigid socket assembly 10 creates a tubular recess which receives a residual limb.

As illustrated in FIG. 2, pivotal rear limb engaging panel 30 overlaps non-pivotal front limb engaging panel 20 on the inside of non-pivotal front limb engaging panel 20. Rigid outer support rib 72 has an inverted T-shape and supports pivotal rear limb engaging panel 30 in front limb engaging panel 20.

In the exemplary embodiment shown, rigid outer support rib 72 is a separate physical component from rear limb engaging panel 30. In other exemplary embodiments, rigid outer support rib 72 may be permanently or temporarily connected with rear limb engaging panel 30. In still further exemplary embodiments, rigid outer support rib 72 may be singly manufactured with rear limb engaging panel 30.

In the exemplary embodiment shown, pivotal rear limb engaging panel 30 is pivoted to exert an even pressure and hold a residual limb in the place against front limb engaging panel 20. In a preferred exemplary embodiment, pivotal rear limb engaging panel 30 pivots at 10-40 degrees. Rear limb engaging member 30 is flexible and narrow as it is compressed in the contour of the more rigid and longer non-pivotal front limb engaging panel 20. Rigid outer support rib 72 provides structure to rear limb engaging member 30.

As illustrated in the exemplary embodiment shown in FIG. 2, deformable inner liner 78 with silicone liner 80 is designed to fit within rigid socket assembly 10 to accommodate the individual and unique features of a residual limb to provide comfort and reduce impact. Silicone liner 80 cushions and conforms to the shape of a residual limb, while deformable inner liner 78 provides additional cushioning and support. In the exemplary embodiment shown, deformable inner liner 78 is made of cushioning material, such as deformable padding, foam, cushioning, gel, rubber or combinations of these materials. In further exemplary embodiments, deformable liner 78 may be malleable, moldable or adjustable to a specifically fit a residual limb.

While in the exemplary embodiment shown, silicone liner 80 is made of silicone, in further exemplary embodiments, silicone liner 80 may be made of any similar material known in the art. In still further exemplary embodiments, the material properties between silicone liner 80 and deformable inner liner 78 may be designed to provide added friction for augmented suspension when modular prosthetic device 100 is firmly buckled around a residual limb.

In yet further exemplary embodiments, silicone liner 80 and deformable inner liner 78 may include a directional resistance material which allows silicone liner 80 to easily engage deformable inner liner 78 but prevents silicone liner 80 from being easily removed or shifted once in deformable inner liner 78. For example, the inner surface of deformable inner liner 78 and outer surface of silicone liner 80 may contain an area, areas, or coating of a directionally resistive material. In still further exemplary embodiments, the outer surface of silicone liner 80 and the inner surface of deformable inner liner 78 may include engaging structures which allow silicone liner 80 to be easily inserted in deformable inner liner 78, but require additional force to remove from deformable inner liner 78.

In some exemplary embodiments, rigid socket assembly 10 and first convex plate base 35 with integrally molded longitudinal curved plate 34 may be modified to accommodate silicone liner 80 with a serrated pin suspension system, such as with the ALPS pin and gel liner suspension system known in the art.

Deformable liner 78 is shown having rear tongue 76 and a contoured front, which are adapted to comfortably receive a residual limb.

In the exemplary embodiment shown, silicone liner 80 also contains suspension straps 81a, 81b (not shown) with suspension strap buckles 82a, 82b (not shown). Suspension strap 81b with suspension strap buckle 82b is symmetrically arranged on the opposite side of silicone liner 80. In some exemplary embodiments, suspension straps 81a, 81b with suspension strap buckle 82a, 82b may be omitted, or additional or different securing components may be used.

Suspension strap buckles 82a, 82b engage corresponding suspension strap buckles 83a, 83b (not shown) on non-pivotal front limb engaging panel 20 to secure silicone sleeve 80 and deformable inner liner 78 to rigid socket assembly 10. In further exemplary embodiments, silicone sleeve 80 may be temporarily or permanently connected to rigid socket assembly 10 through any means known in the art, including clasps, clips, buckles, straps, adhesives, friction-fit components, contours, snaps, or combinations of these or other structures.

As illustrated in FIG. 2, non-pivotal front limb engaging panel 20 and pivotal rear limb engaging panel 30 are secured together around a residual limb by an intricate strap/buckle assembly comprised of buckle 22, looped cable 39, hook-shaped cable protuberances 31a, 31b, 31c and securing strap 74.

Securing strap 74 completely encircles front limb engaging panel 20 and pivotal rear limb engaging panel 30 and secures to rigid socket assembly 10 through securing strap apertures 75a, 75b, 75c (not shown). In the exemplary embodiment shown, securing strap 74 is made of a non-elastic material and serves as a safety strap. In further exemplary embodiments, securing strap 74 may be any material with a buckle or other structure which allows the tension on securing strap 74 to be adjusted. For example, the tension on securing strap 74 may be adjusted using buckles, clasps, clips, snaps or any other structure or combination structures known in the art.

In the exemplary embodiment shown, securing strap aperture 75b creates a hollow opening perpendicular to the longitudinal portion of rigid outer support rib 72. Securing strap 74 is therefore able to pass completely through the longitudinal portion of rigid outer support rib 72. Securing strap aperture 75c (not shown) is symmetrically positioned on the opposite side of front limb engaging panel 20.

Similarly, looped cable 39 is connected on one end to buckle 22 and hook-shaped cable protuberance 31c on the other to partially encircle front limb engaging panel 20 and pivotal rear limb engaging panel 30. Looped cable 39 proceeds from buckle 22 through apertures 33c (not shown), 33b, 33a, and is then looped around one of hook-shaped cable protuberances 31a, 31b, 31c, depending on the size of a residual limb. As illustrated in FIG. 2, cable aperture 33b creates a hollow opening perpendicular to the longitudinal portion of rigid outer support rib 72. Looped cable 39 is therefore able to pass completely through the longitudinal portion of rigid outer support rib 72. Cable aperture 33c (not shown) is symmetrically positioned on the opposite side of front limb engaging panel 20.

In the exemplary embodiment shown, looped cable 39 is made of metal wire with a protective coating, such as rubber or any other moisture- and/or rust-resistant coating known in the art. Looped cable 39 goes through apertures 33a, 33b, 33c (not shown) to minimize the pressure and wear exerted on the ends of non-pivotal front limb engaging panel 20.

Once looped cable 39 is secured around one of hook-shaped cable protuberances 31a, 31b, 31c, buckle 22 is dosed against front limb engaging panel 20 to pull looped cable 39 tight around rigid socket assembly 10. In the exemplary embodiment shown, buckle 22 is a buckle similar to the type traditionally used on ski boots. In further exemplary embodiments, buckle 22 may be any commercially available plastic buckle or assembly which allows leverage and tightening of looped cable 39. In still further exemplary embodiments, buckle 22 may be several buckles or securing components.

As illustrated in FIG. 2, non-pivotal front limb engaging panel 20 also contains base plate bolts 84a, 84b (not shown) and hinge bolt apertures 77a, 77b, 77c, with symmetrically arranged hinge bolt apertures 77d, 77e, 77f (not shown) on the opposite side of front limb engaging panel 20. Hinge bolt apertures 77a, 77b, 77c, and 77d (not shown), 77e (not shown), 77f (not shown) adjustably secure rigid outer support rib 72 and pivotal rear limb engaging panel 30 to non-pivotal front limb engaging panel 20.

Base plate bolts 84a, 84b (not shown) help join non-pivotal front limb engaging panel 20, and therefore a residual limb, to fitted base component 40 (not shown), containing first convex plate base 35 integrally molded longitudinal curved plate 34. Base plate bolts 84a, 84b (not shown) project through base plate apertures 87a, 87b (not shown) in front limb engaging panel 20 and base plate apertures 85a (not shown), 85b (not shown) in fitted base component 40. Base plate aperture sets (e.g., 87a/87b and 85a/85b) are symmetrically positioned on opposite sides of their respective structural components.

Rocker connector bolts 25a, 25b, 25c (not shown) project through radial tubular portions 24a, 24b, 24c (not shown) of central hollow tubular portion 23 to secure integrally molded longitudinal curved plate 34 to concave plate base 36.

Hollow tubular portion 23 contains prosthetic pipe connector 32, which receives prosthetic limb 15, which in the exemplary embodiment shown is a foot. In the exemplary embodiment shown, prosthetic pipe connector 32 is 30 mm in diameter. In further exemplary embodiments, prosthetic pipe connector 32 may have a diameter between 27 and 32 millimeters. Prosthetic limb 15 is secured in hollow tubular portion 23 by set screws 29a, 29b (not shown), which project through set screw apertures 26a, 26b (not shown), and tightening bolt 28 in base clamping protuberances 27a, 27b (not shown).

Also illustrated in FIG. 2 are securing bolts 90a, 90b. Securing bolts 90a, 90b project through securing apertures 91a (not shown), 91b (not shown) in front limb engaging panel 20 and securing apertures 92a (not shown), 92b (not shown) in fitted base component 40 (not shown). Securing strap 74 also contains securing aperture 95 (not shown), which allows securing bolt 90a to vertically lock securing strap 74 in place.

In further exemplary embodiments securing strap 74 may be vertically locked in place by additional bolts or other structures, including, but not limited to, clips, clasps, buttons, or combinations of these and other structures.

Figure 3:
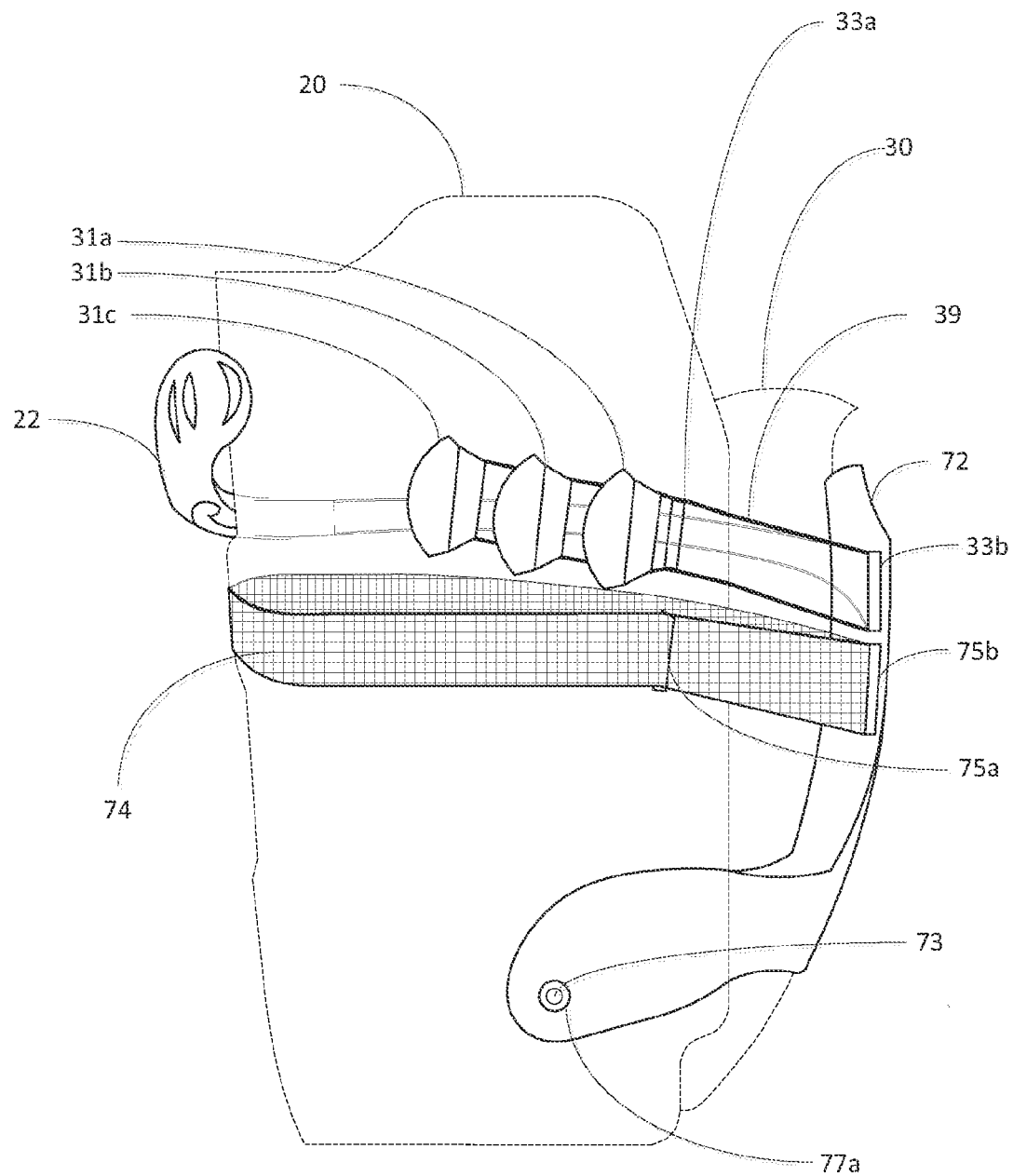
FIG. 3 illustrates an exemplary embodiment of a buckle cable system and hinge for a rapid fit modular prosthetic device for accommodating gait alignment and residual limb shape and volume.

FIG. 3 is an exemplary embodiment of a buckle/cable system of rigid socket assembly 10. The buckle/cable system secures non-pivotal front limb engaging panel 20, pivotal rear limb engaging panel 30 and rigid outer support rib 72 around a residual limb. In the exemplary embodiment shown, non-pivotal front limb engaging panel 20 and pivotal rear limb engaging panel 30 are shown in phantom to better view the components of the buckle/cable system.

As illustrated in FIG. 3, looped cable 39 is attached at one end to buckle 22. Looped cable 39 proceeds around the outside of non-pivotal front limb engaging panel 20 and goes through cable aperture 33c (not shown) on the opposite side of front limb engaging panel 22, and then passes through cable aperture 33b in rigid outer support rib 72. Looped cable 39 continues around the rear of rigid socket assembly 10 and passes through cable aperture 33a in non-pivotal front limb engaging panel 20. In the exemplary embodiment shown, looped cable 39 is looped around hook-shaped cable protuberance 31c, but in further exemplary embodiments, may be looped around any one of hook-shaped cable protuberances 31a, 31b, 31c, depending on the size of a residual limb. Buckle 22 tightens against no pivotal front limb engaging member 20 to tighten looped cable 39.

In the exemplary embodiment shown, securing strap 74 is a non-elastic component completely encircling rigid socket assembly 10. Securing strap 74 passes around the exterior of pivotal rear limb engaging panel 30 by passing through securing strap apertures 75c (not shown), 75b, 75a. Cable apertures 33a, 33b, 33c (not shown) and securing strap apertures 75a, 75b, 75c (not shown) allow looped cable 39 and securing strap 74 to tighten around rigid socket assembly 10 without putting excess pressure and strain on the edges of non-pivotal front limb engaging panel 20.

In further exemplary embodiments, rigid socket assembly 10 may contain more or fewer securing cables/straps, and securing cables or straps may have selective or continual adjustability around rigid socket assembly 10. For example, additional hook-shaped cable protuberances 31 may be available for looped cable 39. Additional tightening components, such as buckles, clasps, clips, snaps or any other structure or combination of structures, may be used to provide additional adjustment to looped cable 39 or securing strap 74.

In still further exemplary embodiments, rigid outer support rib 72 may contain additional apertures for looped cable 39 or securing strap 74.

In the exemplary embodiment shown, rigid outer support rib 72 has an inverted T-shape and is rigid to provide structural support for flexible rear limb engaging panel 30. Hinge bolt 73 projects through hinge bolt aperture 77a on front limb engaging panel 20, and corresponding hinge bolt apertures 17a and 18a on rear limb engaging panel 30 and rigid outer support rib 72, respectively, to attach rigid outer support rib 72 and rear limb engaging panel 30 to non-pivotal front limb engaging panel 20.

Hinge bolt 73 projects through one of hinge bolt apertures 77a, 77b (not shown), 77c (not shown), depending on the size of a residual limb. As illustrated in the exemplary embodiment shown in FIG. 3, the horizontal portion of T-shaped rigid outer support rib 72 extends against the interior of non-pivotal front limb engaging panel 20.

Rigid socket assembly 10 also contains symmetrically arranged hinge bolt apertures 77d (not shown), 77e (not shown), 77f (not shown) on the opposite side of front limb engaging panel 20, as well as symmetrically arranged hinge bolt apertures 17b (not shown), 18b (not shown) in rear limb engaging panel 30 and rigid outer support rib 72, respectively. A second hinge bolt 73 (not shown) secures rear limb engaging panel 30 and rigid outer support rib 72 to one of hinge bolt apertures 77d (not shown), 77e (not shown), 77f (not shown).

Figure 4:
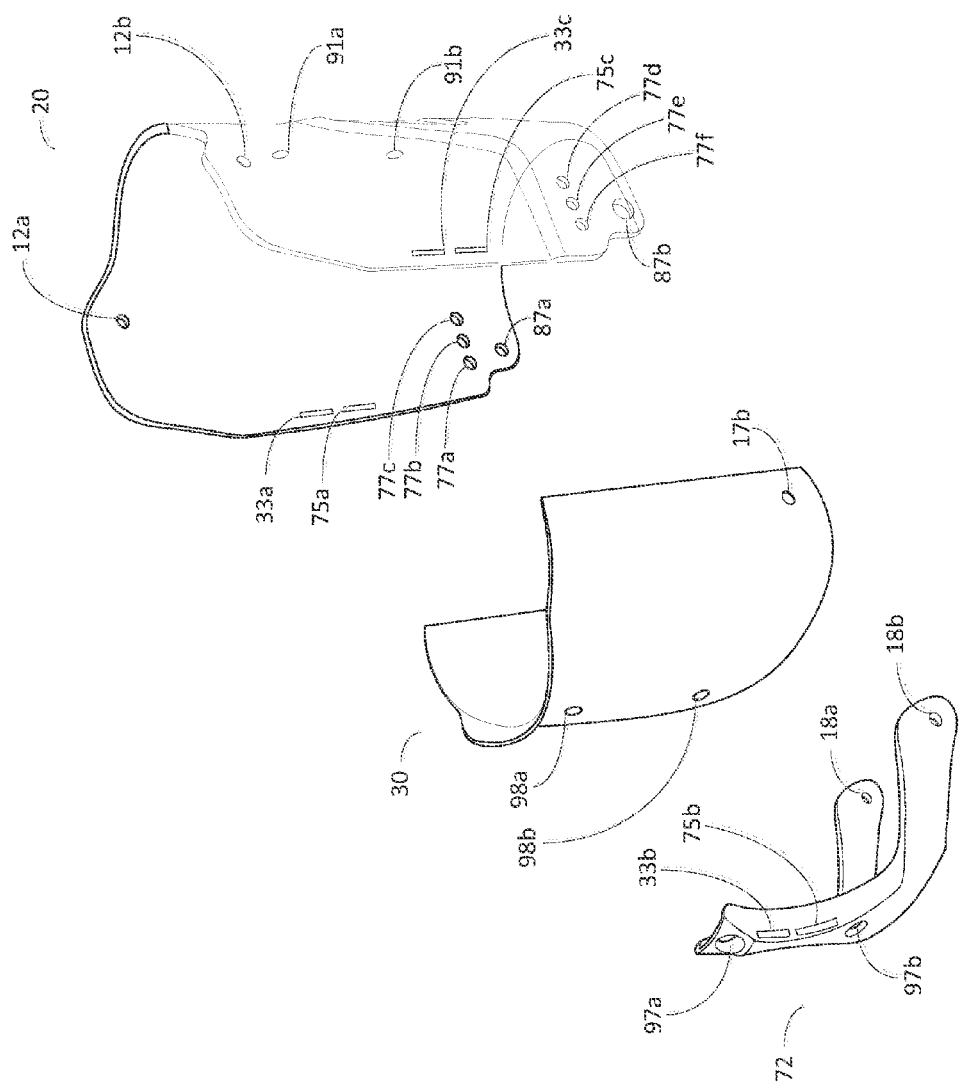
FIG. 4 illustrates an exemplary embodiment of a rigid socket assembly for a rapid fit modular prosthetic device for accommodating gait alignment and residual limb shape and volume.

FIG. 4 is an exploded view of rigid socket assembly 10. Non-pivotal front limb engaging panel 20 is shown separated from pivotal rear limb engaging panel 30 and rigid outer support rib 72. Cable apertures 33a, 33b, 33c and securing strap apertures 75a, 75b, 75c are shown without looped cable 39 (not shown) and securing strap 74 (not shown).

In the exemplary embodiment shown, rigid outer support rib 72 is a separate physical component from rear limb engaging panel 30, which securely attaches to rear limb engaging panel 30 by attachment means, such as screws or bolts, at attachment apertures 97a, 97b on rigid outer support rib and 98a, 98b on rear limb engaging panel 30. In other exemplary embodiments, rigid outer support rib 72 and rear limb engaging panel 30 may be attached by alternative structures, including, but not limited to, molding, adhesives, clips, claps, contours, or combinations of these and other attachment means.

Rigid outer support rib 72 also contains hinge bolt apertures 18a, 18b, wh ch correspond to hinge bolt apertures 17a, 17b on rear limb engaging panel 30 and hinge bolt apertures 77a, 77b, 77c, 77d, 77e, 77f on front limb engaging panel 20. Hinge bolts 73a (not shown), 73b (not shown) engage hinge bolt aperture sets 17a/18a and 17b/18b, respectively, to adjustably and pivotally secure rigid outer support rib 72 and rear limb engaging panel 30 to front limb engaging panel 20.

Hinge bolts 73a (not shown), 73b (not shown) engage one of hinge bolt apertures 77a, 77b, 77c and 77d, 77e, 77f, respectively.

In some exemplary embodiments, hinge bolts 73a (not shown), 73b (not shown) may engage symmetric hinge bolt apertures on front limb engaging panel 20. For example, hinge bolt 73a (not shown) ray engage hinge bolt aperture 77a and hinge bolt 73b (not shown) may engage hinge bolt aperture 77f. In further exemplary embodiments, hinge bolts 73a (not shown), 73b (not shown) may engage non-symmetric hinge bolt apertures, such as 77a and 77e, respectively.

In some exemplary embodiments, hinge bolts 73a (not shown), 73b (not shown) may permanently secure rigid outer support rib 72, rear limb engaging panel 30 and front limb engaging panel 20. In other exemplary embodiments, hinge bolts 73a (not shown), 73b (not shown) may allow for selective adjustment of rigid outer support rib 72, rear limb engaging panel 30 and front limb engaging panel 20.

Base plate bolts 84a (not shown), 84b (not shown) engage base plate apertures 87a, 87b, respectively, to securely fasten front limb engaging panel 20 to fitted base component 40.

Also illustrated in FIG. 4 are attachment points 12a, 12b for suspension strap buckles 83a (not shown), 83b (not shown).

FIGS. 5a, 5b and 5c illustrate the adjustability of rigid socket assembly 10 to accommodate residual limbs of various sizes. In FIG. 5a, rigid socket assembly 10 is at its smallest size. Pivotal rear limb engaging panel 30 is recessed within front limb engaging panel 20, such that hinge bolt 73 projects through hinge bolt aperture 77c. FIG. 5b illustrates rigid socket assembly 10 with hinge bolt 73 projecting through hinge bolt aperture 77b, and FIG. 5c illustrates rigid socket assembly 10 with hinge bolt 73 projecting through hinge bolt aperture 77a.

While FIGS. 5a, 5b and 5c illustrate a single side of rigid socket assembly 10, it should be understood that front limb engaging panel 20 contains symmetrical hinge bolt apertures which are similarly engaged by a hinge bolt.

While in the exemplary embodiment illustrated in FIGS. 5a, 5b and 5c, the adjustability of rigid socket assembly 10 is limited to three pre-determined sizes, in further exemplary embodiments, additional hinge bolt apertures 77 may be provided for additional adjustability. In still further exemplary embodiments, a structure other than a hinge bolt may be used to provide continuous adjustability.

Figure 6A:
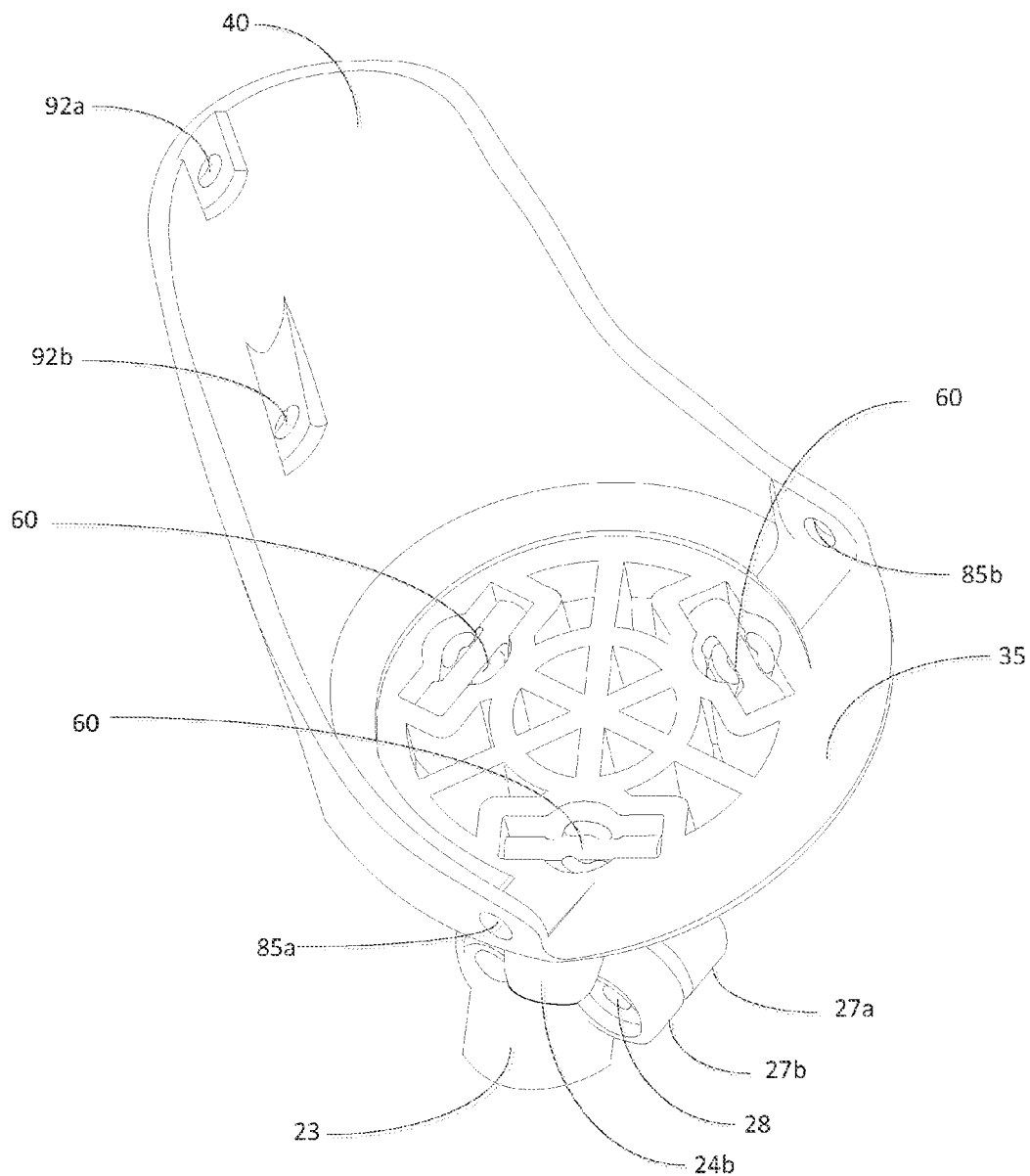
FIG. 6a illustrates an exemplary embodiment of a base component assembly for a rapid fit modular prosthetic device for accommodating gait alignment and residual limb shape and volume.
Figure 6B:
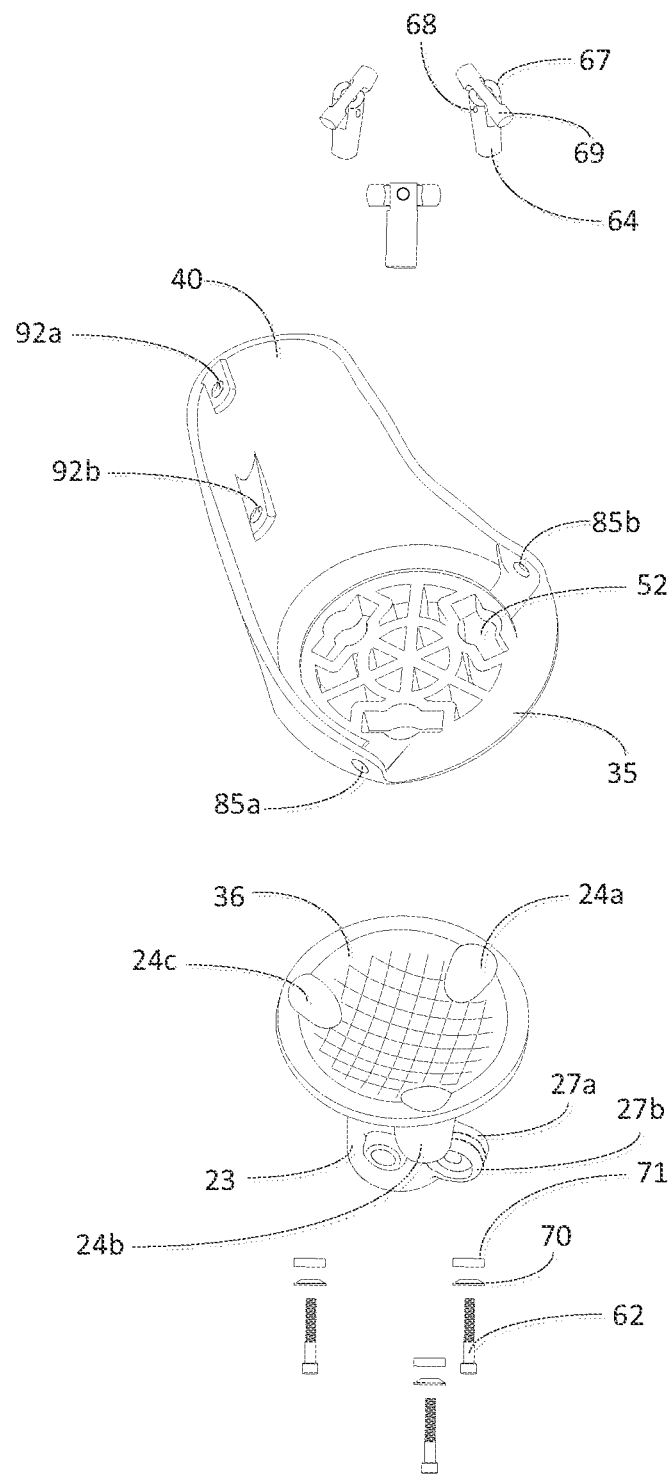
FIG. 6b illustrates an exploded view of an exemplary embodiment of a base component assembly for a rapid fit modular prosthetic device for accommodating gait alignment and residual limb shape and volume.

FIGS. 6a and 6b show the construction of an exemplary fitted base component 40. FIG. 6a illustrates an assembled fitted base component 40, with first convex plate 35 and rocker bolt assemblies 60 visible. As illustrated in FIG. 6a, convex plate 35 is an integral component with fitted base component 40 and is the top surface of fitted base component 40.

Rocker bolt assemblies 60 engage radial tubular portions 24a (not shown), 24b, 24c (not shown). Base plate bolts 84a (not shown), 84b (not shown) project through base plate apertures 85a, 85b to secure non-pivotal front limb engaging panel 20 (not shown) to fitted base component 40. When assembled, base plate apertures 85a, 85b align with base plate apertures 87a (not shown), 87b (not shown) of front limb engaging panel 20 (not shown).

Securing apertures 92a, 92b are adapted to receive securing bolts 90a (not shown), 90b (not shown), respectively, to secure fitted base component 40 to front limb engaging panel 20 (not shown).

In the exemplary embodiment shown, first convex plate 35 is constructed of a weight-bearing material.

Also illustrated in FIG. 6a are base clamping protuberances 27a, 27b with tightening bolt 28. Tightening bolt 28 pulls base clamping protuberances 27a, 27b closer together to tightly engage the pipe of a prosthetic device. In the exemplary embodiment shown, base clamping protuberances 27a, 27b are specifically designed to remain approximately 28-32 mm apart after tightening bolt 28 is tightened.

FIG. 6b is an exploded view of an exemplary fitted base component 40. Rocker bolt assemblies 60 are made of hollow threaded socket 64 with u-shaped upper portion 67 adapted to receive contoured horizontal rod 69, threaded hex bolt component 62 with convex collar washer 70 and concave funnel-shaped washer 71, and pivot pin 68. Pivot pin 68 is shown on hollow threaded socket 64 and secure contoured horizontal rod 69 to hollow threaded socket 64. Rocker bolt assemblies 60 rest in rocker bolt apertures 52 of first convex plate 35 and are unable to fall through rocker bolt apertures 52 because of contoured horizontal rod 69.

Hollow threaded socket 64 projects into radial tubular portions 24a, 24b, 24c of concave base plate 36, allowing threaded hex bolt component 62 to tighten within hollow threaded socket 64. Convex collar washer 70 and concave funnel-shaped washer 71 are secured between hollow threaded socket 64 and threaded hex bolt component 62.

In the exemplary embodiment shown, there are three rocker bolt assemblies 60, and radial tubular portions 24a (not shown), 24b, 24c (not shown), with corresponding rocker bolt apertures 52, are symmetrically arranged around concave base plate 36 and first convex plate base 35, respectively. In further exemplary embodiments, additional rocker bolt assemblies 60 may be used, and radial tubular portions 24 and rocker bolt apertures 52 may be unevenly distributed around the perimeter of concave base plate 36 and first convex plate base 35.

Base plate apertures 85a, 85b and securing bolt apertures 92a, 92b are also shown in fitted base component 40. Base plate bolts 84a, 84b (not shown) project through base plate apertures 85a, 85b and corresponding base plate apertures 87a (not shown), 87b (not shown) on non-pivotal front limb engaging panel 20 (not shown) to secure non-pivotal front limb engaging panel 20 (not shown) to fitted base component 40. Similarly, securing bolts 90a (not shown), 90b (not shown) project through securing bolt apertures 91a (not shown), 91b (not shown) on non-pivotal front limb engaging panel 20 and securing bolt apertures 92a, 92b to provide additional support in securing fitted base component 40 to rigid socket assembly 10 (not shown).

Rocker bolt assemblies 60 secure first convex plate base 35 to concave plate base 36. In the exemplary embodiment shown, concave plate base 36 is adapted to receive the lower surface of first convex plate base 35.

Figure 7A:
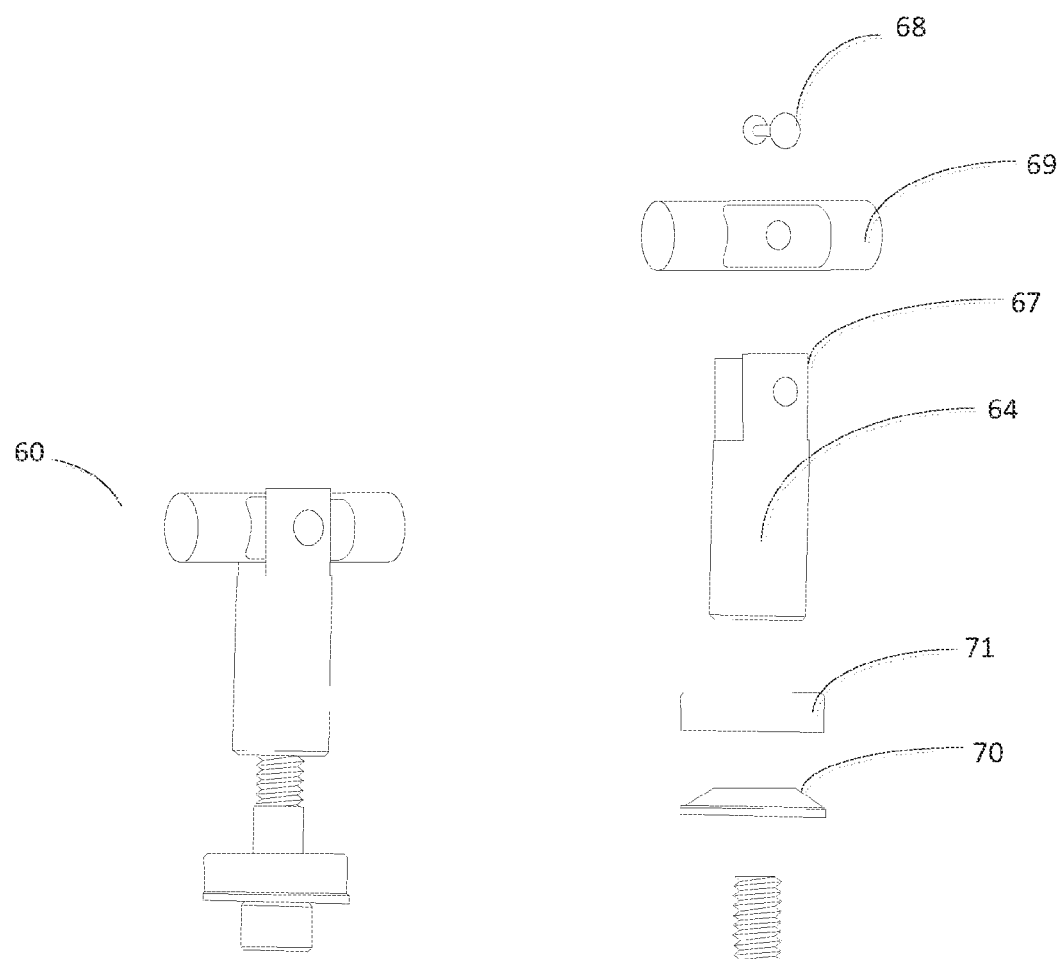
FIG. 7a illustrates an exemplary embodiment of a rocker bolt assembly.
Figure 7B:
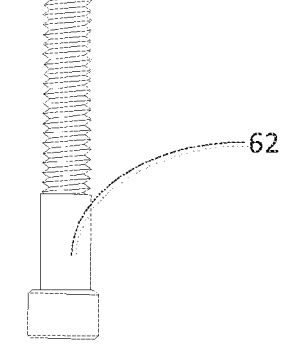
FIG. 7b illustrates an exploded view of an exemplary embodiment of a rocker bolt assembly.

FIGS. 7a and 7b illustrate an exemplary rocker bolt assembly 60 in more detail. As illustrated, rocker bolt assembly 60 is comprised of pivot pin 68, contoured horizontal rod 69, hollow threaded socket 64 with u-shaped upper portion 67, concave funnel-shaped washer 71, convex collar washer 70 and threaded hex bolt component 62.

Pivot pin 68 pivotally secures contoured horizontal rod 69 to hollow threaded socket 64. Contoured horizontal rod 69 is therefore allowed to pivot relative to hollow threaded socket 64. In the exemplary embodiment shown, horizontal rod 69 can pivot up to 20 degrees relative to hollow threaded socket 64. Threaded hex bolt component 62 screws into hollow threaded socket 64, with concave funnel-shaped washer 71 and convex collar washer 70 secured between threaded hex bolt component 62 and hollow threaded socket 64. The construction of rocker bolt assembly 60 allows for limited movement between first convex base plate 35 and concave base plate 36.

In further exemplary embodiments, contoured horizontal rod 69 may be secured to hollow threaded socket 64 with a different securing structure. For example, contoured horizontal rod 69 may be friction fit or use a spring-pin mechanism or other structure which may pivotally secure horizontal rod 69 to hollow threaded socket 64. Different constructions of rocker bolt assemblies 60 may allow for increased movement or pivoting.

Figure 8A:
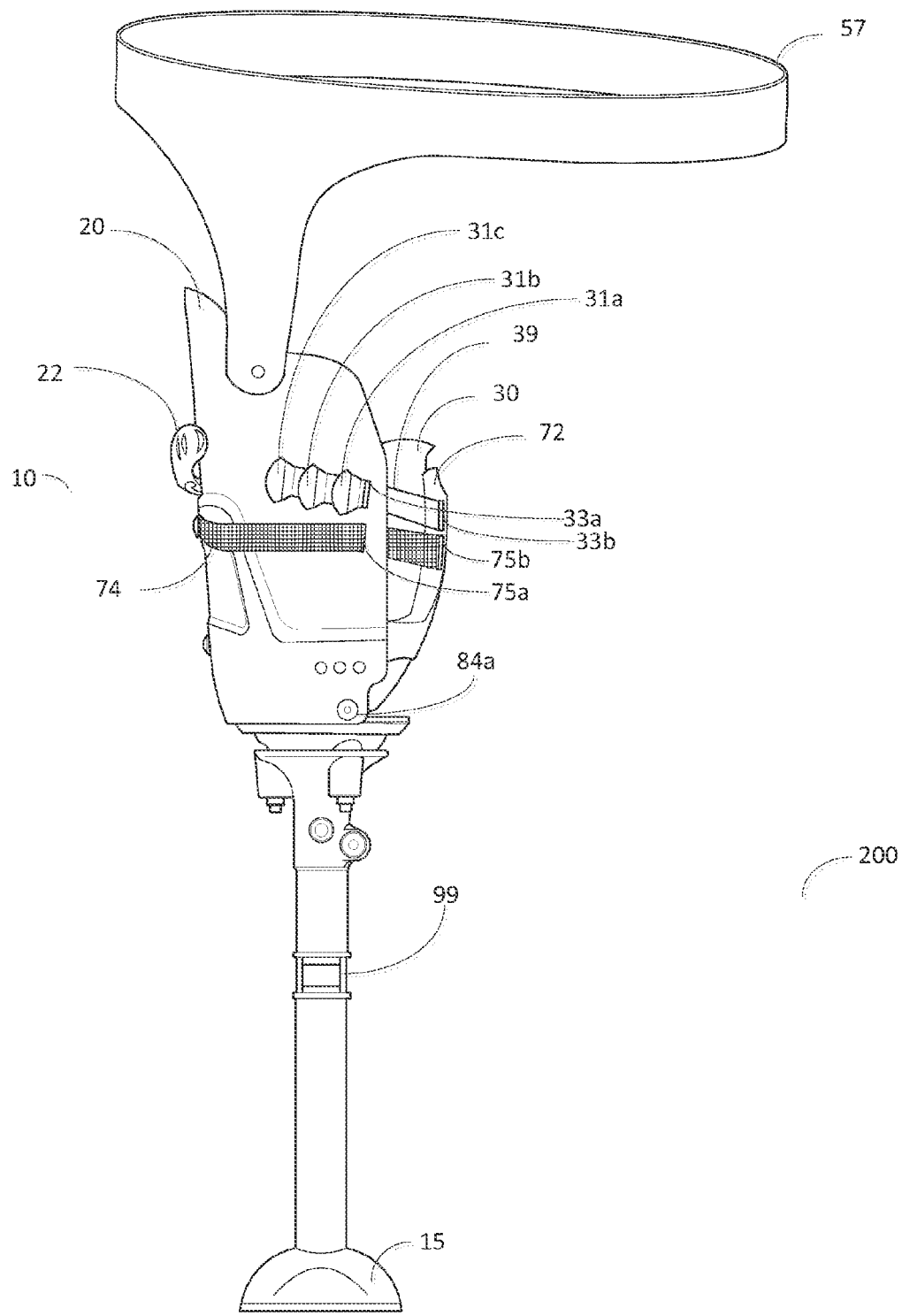
FIG. 8a is an exemplary embodiment of a rapid fit modular prosthetic device for accommodating gait alignment and residual limb shape and volume for an above-the-knee residual limb.

FIG. 8a illustrates an exemplary embodiment of rapid fit modular prosthetic device for accommodating gait alignment and residual limb shape and volume adapted for an above-the-knee residual limb 200. As illustrated, rapid fit modular prosthetic device for accommodating gait alignment and residual limb shape and volume for an above-the-knee residual limb 200 is very similar to rapid fit modular prosthetic device for accommodating gait alignment and residual limb shape and volume for a below-the-knee residual limb 100. However, the components of rigid socket assembly 10 may be larger to accommodate the larger size of an above-the-knee residual limb, and prosthetic device 15 includes knee 99. The entire rapid fit modular prosthetic device for accommodating gait alignment and residual limb shape and volume 200 is also rotated 90 degrees compared to the orientation for a below-the-knee residual limb.

Rapid fit modular prosthetic device for accommodating gait alignment and residual limb shape and volume 200 also includes waist strap 57 to help stabilize and secure rapid fit modular prosthetic device for accommodating gait alignment and residual limb shape and volume 200.

In the exemplary embodiment illustrated in FIG. 8a, front limb engaging panel 20 and rigid outer support rib 72 are larger to accommodate a larger residual limb. Front limb engaging panel 20, specifically, needs to be taller in order to properly secure an above-the-knee residual limb. In the exemplary embodiment shown, non-pivotal front limb engaging panel 20 is 6 cm higher. Because of the way pressure is exerted on rapid fit modular prosthetic device for accommodating gait alignment and residual limb shape and volume 200 by an above-the-knee residual limb, additional stabilizing is needed by front limb engaging panel 20. In other exemplary embodiments, rigid outer support rib 72 may be larger or of a more flattened shape to reduce projection between the legs.

In some exemplary embodiments, cable apertures 33a, 33b and securing strap apertures 75a, 75b may be positioned differently on front limb engaging panel 20 and rigid outer support rib 72 to create additional stability in securing rapid fit modular prosthetic device for accommodating gait alignment and residual limb shape and volume 200 to a larger residual limb.

As illustrated, rapid fit modular prosthetic device for accommodating gait alignment and residual limb shape and volume 200 contains an intricate strap/buckle system identical to that of rapid fit modular prosthetic device for accommodating gait alignment and residual limb shape and volume 100. However, in further exemplary embodiments, rapid fit modular prosthetic device for accommodating gait alignment and residual limb shape and volume 200 may contain additional looped cables 39, securing straps 74, buckles 22 or other securing members.

In the exemplary embodiment shown, looped cable 39 is looped around hook-shaped cable protuberance 31b, which creates a larger volume inside the recess created by non-pivotal front limb engaging panel 20 and pivotal rear limb engaging panel 30. In further exemplary embodiments, looped cable 39 may be secured using any of hook-shaped cable protuberances 31a, 31b, 31c.

Figure 8B:
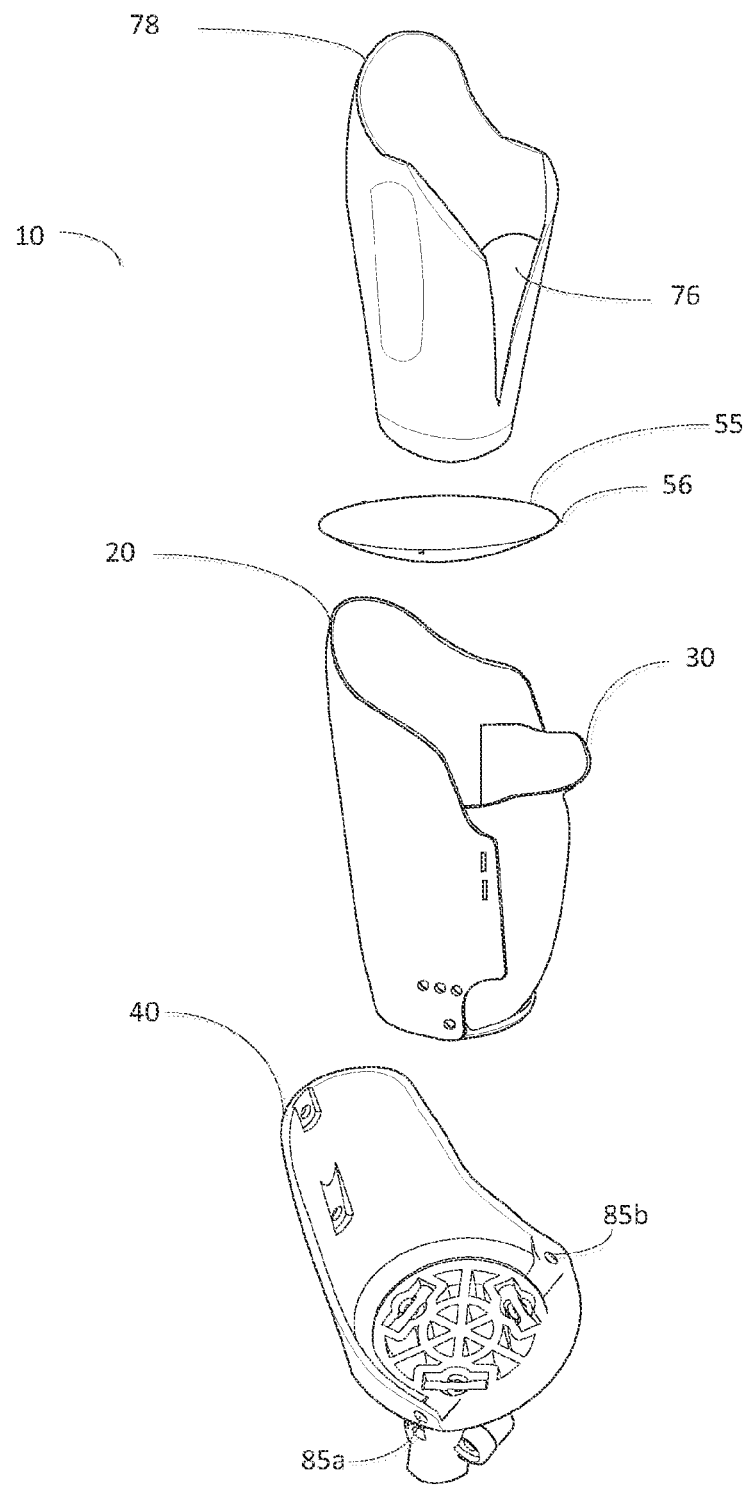
FIG. 8b is an exploded view of the above-the-knee components of an exemplary rapid fit modular prosthetic device for accommodating gait alignment and residual limb shape and volume.

FIG. 8b illustrates additional differences between rapid fit modular prosthetic device for accommodating gait alignment and residual limb shape and volume for above-the-knee residual limbs 200 and rapid fit modular prosthetic device for accommodating gait alignment and residual limb shape and volume 100 for below-the-knee residual limbs.

As illustrated, deformable inner liner 78 with rear tongue 76 does not contain a silicone liner. In further exemplary embodiments, deformable inner liner 78 may contain or utilize a liner made of silicone or other similar materials. Support cup 55, with support cup connectors 56, is inserted in rigid socket assembly 10 under deformable liner 78 to provide height adjustments.

In below-the-knee embodiments, the distance from a user's residual limb to the bottom of the prosthetic device is adjusted by the length of the pipe on the prosthetic device. However, in above-the-knee embodiments, the distance from a user's residual limb to the prosthetic knee must also be adjusted. Support cup 55 may be placed at any height in the tubular recess created by rigid socket assembly 10 to support a user's residual limb at the necessary height.

Support cup connectors 56 engage the interior surface of non-pivotal front limb engaging member 20 to secure support cup 55. In the exemplary embodiment shown, support cup connectors 56 are screws which are screwed to both front limb engaging member 20 and rear limb engaging member 30. However, in further exemplary embodiments, support cup connectors 56 may be any securing structure or device known in the art, including, but not limited to, clips, clasps, braces, brackets, bolts, adhesives, friction-fit components, contours, and combinations of these and other structures. In still further exemplary embodiments, support cup 55 may be permanently, releasably or adjustably secured to rigid socket assembly 10.

In the exemplary embodiment shown, base plate apertures 85a, 85b are visible on both non-pivotal front limb engaging panel 20 and fitted base component 40. Base plate bolts 84a, 84b (not shown) project through base plate apertures 85a, 85b to secure non-pivotal front lamb engaging panel 20 to fitted base component 40.

Figure 9:
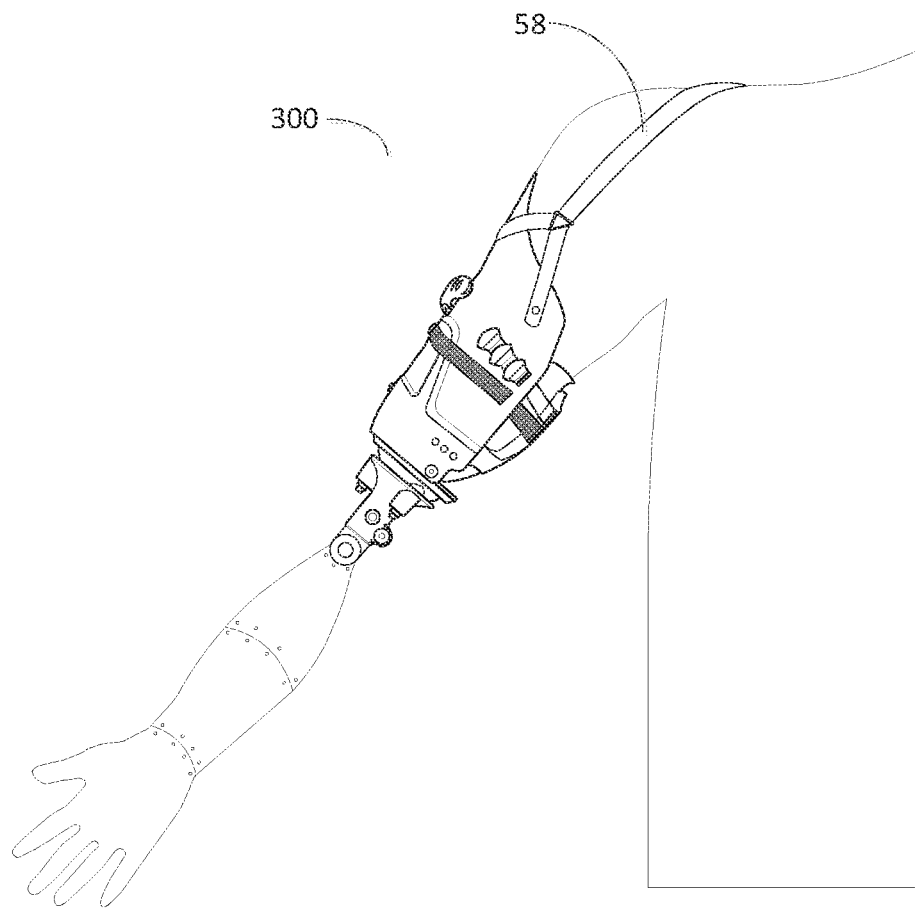
FIG. 9 illustrates an exemplary embodiment of a rapid fit modular prosthetic device for accommodating gait alignment and residual limb shape and volume adapted for use on arm-related residual limbs.

FIG. 9 illustrates rapid fit modular prosthetic device for accommodating gait alignment and residual limb shape and volume for use on a residual limb which is an arm 300. As illustrated, rapid fit modular prosthetic device for accommodating gait alignment and residual limb shape and volume 300 contains basically identical structures as rapid fit modular prosthetic device for accommodating gait alignment and residual limb shape and volume for a below-the-knee residual limb 100 and rapid fit modular prosthetic device for accommodating gait alignment and residual limb shape and volume for an above-the-knee residual limb 200. However, in the exemplary embodiment illustrated, rapid fit modular prosthetic device for accommodating gait alignment and residual limb shape and volume 300 includes shoulder strap 58 to secure rapid fit modular prosthetic device for accommodating gait alignment and residual limb shape and volume 300 to a residual limb which is an arm.

What is claimed is:
1. A rapid fit modular prosthetic apparatus comprised of:
a rigid socket assembly comprising
a front limb engaging panel containing at least two base plate apertures and plurality of hinge bolt apertures,
a pivotal rear limb engaging panel to securely enclose a residual limb, said pivotal rear limb engaging panel containing at least one hinge bolt aperture which adjustably corresponds to at least one of said plurality of hinge bolt apertures in said front limb engaging panel,
a rigid outer support rib containing at least one hinge bolt aperture corresponding to said at least one hinge bolt aperture of said pivotal rear limb engaging panel,
wherein said front limb engaging panel, said pivotal rear limb engaging panel and said rigid outer support rib create a tubular recess,
a deformable liner having a rear tongue and a contoured front adapted to receive a residual limb, wherein said deformable liner is contoured to fit within said tubular recess, and
at least one hinge bolt which engages said at least one hinge bolt aperture on said rigid outer support rib, said at least one corresponding hinge bolt aperture on said pivotal rear limb engaging panel and one of said plurality of hinge bolt apertures on said front limb engaging panel;
a securing strap assembly comprising
a looped cable attached at a first end to a buckle,
a plurality of hook-shaped cable protuberances adapted to receive a second end of said looped cable, wherein said looped cable passes through at least one cable aperture in said rigid outer support rib and at least one cable aperture in said front limb engaging panel,
at least one securing strap, wherein said securing strap passes through at least one securing strap aperture in said rigid outer support rib and at least one securing strap aperture in said front limb engaging panel and completely encircles said rigid socket assembly;
a fitted base component comprising
a first convex plate base having a plurality of rocker bolt apertures, wherein the lower surface of said first convex plate base is a longitudinal curved plate,
at least two base plate apertures corresponding to said at least two base plate apertures of said front limb engaging panel,
a concave base plate with an upper surface adapted to receive said longitudinal curved plate and a plurality of radial tubular portions corresponding to said rocker bolt apertures, and
a hollow tubular portion adapted to receive a prosthetic pipe containing at least two base clamping protuberances and at least one set screw aperture;
a plurality of rocker bolt assemblies, each of said rocker bolt assemblies comprising
a hollow threaded socket with a u-shaped upper portion containing an aperture,
a contoured horizontal rod with an aperture, wherein said contoured horizontal rod is secured within u-shaped upper portion by a pivot pin extending through said aperture in said u-shaped upper portion and said aperture in said horizontal rod,
a threaded hex bolt component,
a concave funnel-shaped washer, and
a convex collar washer,
wherein said hollow threaded socket projects through one of said rocker bolt apertures to engage said threaded hex bolt component projecting upward through one of said radial tubular portions so that said concave funnel-shaped washer and said convex collar washer are secured between said hex bolt component and the lower surface of said radial tubular portion;
at least two base plate screws adapted to engage said base plate apertures and secure said front limb engaging panel and said fitted base component;

at least one set screw which engages said set screw aperture;
at least one tightening bolt engaging said base clamping protuberances to tighten said tubular hollow portion around said prosthetic pipe.

2. The rapid fit modular prosthetic apparatus of claim 1 wherein said deformable liner further includes a silicone sleeve.

3. The apparatus of claim 2 wherein said silicone sleeve includes at least one suspension strap with a first buckle end and said front limb engaging panel includes a second buckle end corresponding to said first buckle end.

4. The rapid fit modular prosthetic apparatus of claim 1 wherein said looped cable contains a protective coating selected from the group consisting of a moisture-resistant coating, a rust-resistant coating, and combinations thereof.

5. The apparatus of claim 1 wherein said deformable liner is made of a material selected from the group consisting of deformable padding, foam, cushioning, gel, rubber and combinations thereof.

6. The apparatus of claim 1 wherein said pivotal rear limb engaging panel pivots at 10-40 degrees.

7. The apparatus of claim 1 which further includes a prosthetic pipe connector having a diameter between 27 and 32 millimeters.

8. The apparatus of claim 1 which further includes a prosthetic pipe connector having a diameter of 30 millimeters.

9. The apparatus of claim 1 which further includes a waist strap.

10. The apparatus of claim 1 which further includes a shoulder strap.

11. The apparatus of claim 1 having three hook-shaped cable protuberances.

12. The apparatus of claim 1 wherein said rigid outer support rib has an inverted T-shape.

13. The apparatus of claim 12 wherein said rigid outer support rib overlaps said front limb engaging panel on the interior of said front limb engaging panel.

14. The apparatus of claim 12 wherein said rigid outer support rib contains two symmetrically arranged hinge bolt apertures on the horizontal portion of said inverted T-shape rigid outer support rib and said rear limb engaging panel contains two symmetrically arranged hinge bolt apertures corresponding to said hinge bolt apertures on said rigid outer support rib.

15. The apparatus of claim 1 wherein said rigid outer support rib contains at least one attachment aperture and said rear limb engaging panel contains at least one corresponding attachment aperture, wherein at least one attachment member engaging said attachment apertures to secure said rigid outer support rib to said rear limb engaging panel.

16. The apparatus of claim 1 wherein said base clamping protuberances remain 28 to 32 millimeters apart when said tightening bolt is tightened.

17. The apparatus of claim 1 wherein said contoured horizontal rod of said rocker bolt assemblies pivots up to 20 degrees relative to said hollow threaded socket portion.

18. The apparatus of claim 1 wherein said front limb engaging panel is non-pivotal.

19. The apparatus of claim 1 which further contains a support cup.

20. The apparatus of claim 1 wherein said securing strap includes at least one vertical position securing component.

* * * * *

UNITED STATES PATENT AND TRADEMARK OFFICE
CERTIFICATE OF CORRECTION

PATENT NO. : 8,470,050 B2
APPLICATION NO. : 13/274130
DATED : June 25, 2013
INVENTOR(S) : Timothy R. Dillingham It is certified that error appears in the above-identified patent and that said Letters Patent is hereby corrected as shown below:

In the Specification:

Column 3, line 17 – "A rapid fit nodular" should read as "A rapid fit modular"

Column 3, line 57 – "reference numerals in the varios" should read as "reference numerals in the various"

Column 4, line 22 – "rapid fit nodular" should read as "rapid fit modular"

Column 6, line 53 – "buckle 22 is dosed" should read as "buckle 22 is closed"

Column 8, line 61 – "wh ch correspond" should read as "which corresponds"

Column 9, line 7 – "ray engage hinge bolt" should read as "may engage hinge bolt"

Signed and Sealed this
Twenty-sixth Day of November, 2013

Margaret A. Focarino
*Commissioner for Patents of the United States Patent and Trademark Office*